United States Patent [19]

Hauser

[11] Patent Number: 4,640,688
[45] Date of Patent: Feb. 3, 1987

[54] URINE COLLECTION CATHETER

[75] Inventor: Thomas M. Hauser, Sanibel, Fla.

[73] Assignee: Mentor Corporation, Minneapolis, Minn.

[21] Appl. No.: 768,633

[22] Filed: Aug. 23, 1985

[51] Int. Cl.$^4$ ............................................. A61F 44/00
[52] U.S. Cl. ................................... 604/352; 604/180
[58] Field of Search ............................... 604/346–353, 604/180; 128/132 R

[56] References Cited

U.S. PATENT DOCUMENTS 2,305,453 12/1942 Martos ........................... 604/346 X
4,540,409 9/1985 Nystrom et al. ................... 604/349

FOREIGN PATENT DOCUMENTS 520401 3/1931 Fed. Rep. of Germany ...... 604/347
1595711 8/1981 United Kingdom ............... 604/349
2075847 11/1981 United Kingdom ............... 604/349

Primary Examiner—Dalton L. Truluck
Attorney, Agent, or Firm—Kinney & Lange

[57] ABSTRACT

A urine collection catheter having a tubular portion open at its outer end and designed to be connected to a urine receptacle and a cup or cone shaped portion integrally connected to the inner end of said tubular portion, the cup shaped portion being of a shape to conform generally with that of the tip or head or glans of a typical penis. The cup shaped portion has a pressure sensitive adhesive on the inner surface to enable the catheter to adhere to the head of a penis when the catheter is pressed into engagement with the penis. The cup shaped portion is conical and is connected to the tubular member by a bulbous portion to receive surges of urine. In one version, the thickness of the cup shaped portion decreases from its outer to its inner end.

6 Claims, 5 Drawing Figures

U.S. Patent     Feb. 3, 1987     4,640,688
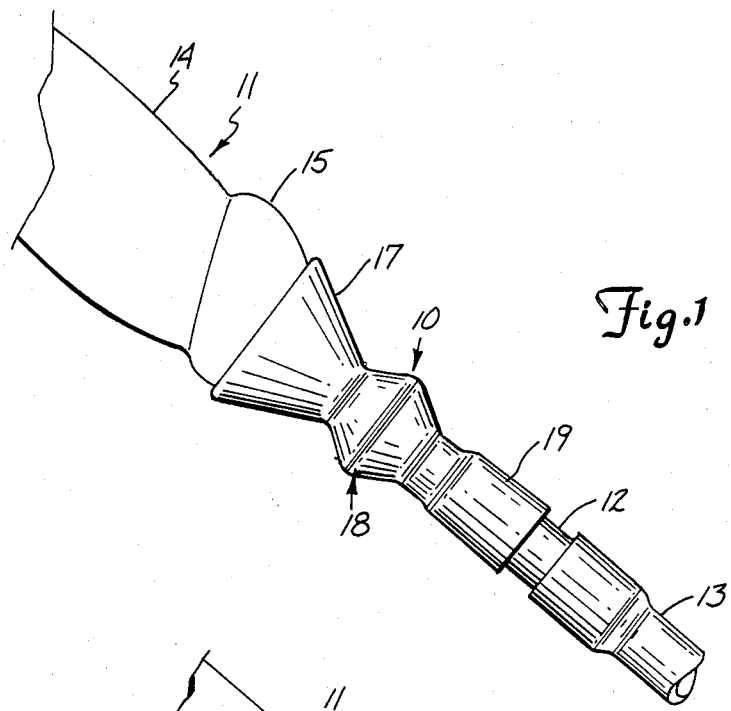
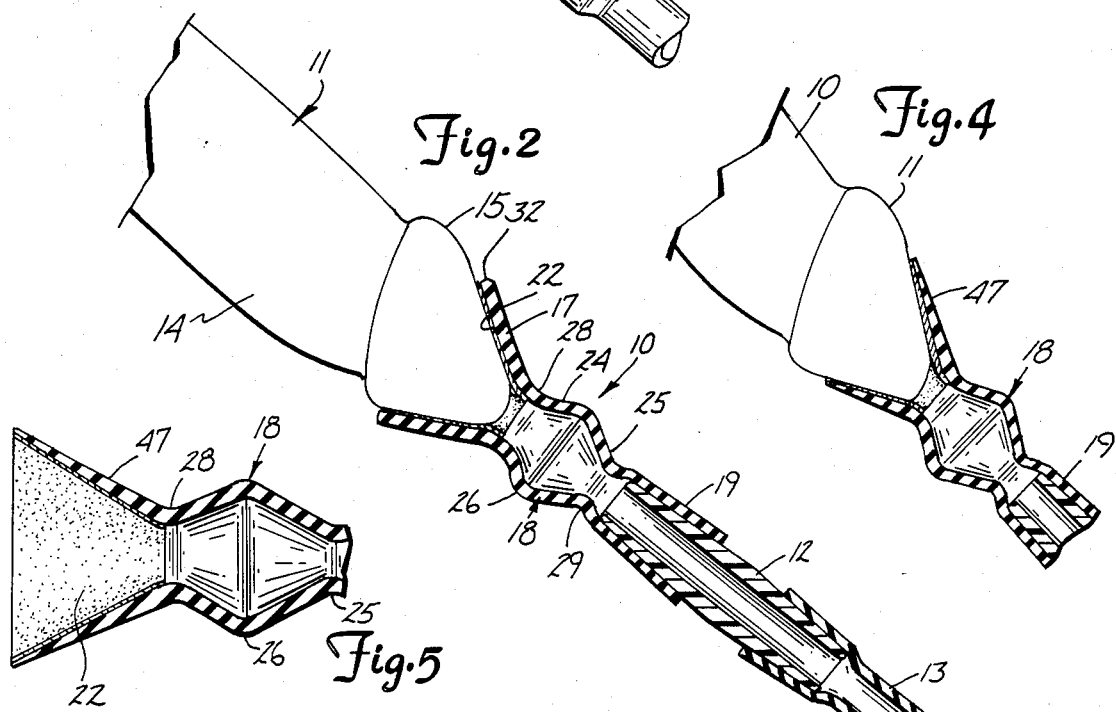

URINE COLLECTION CATHETER

SUBJECT MATTER OF THE INVENTION

The present invention is concerned with a urine collection catheter having a cup shaped portion which is adhesively secured to the tip of the penis.

BACKGROUND OF THE INVENTION

1. Field of the Invention

It is common in connection with people who are severely incontinent, to apply a male urinal catheter consisting of a sheath of flexible material placed over the penis and connected to a urine receptacle with a tube or other flexible conduit. The urine receptacle may be worn on the body or near the body. The problem with such devices is to make them liquid tight and at the same time comfortable to the wearer, since they must be worn for long periods of time. One initial approach to the problem was to use a tape wound around the outside of a sheath designed like a condom. This tended, however, to produce constrictions and discomfort.

In the Hauser U.S. Pat. No. 4,187,851, a double faced adhesive tape of rather soft deformable material is wound around the penis before the condom-like sheath is applied. This acts as a cushion so that the sheath does not constrict the penis. At the same time, it aids in forming a liquid-tight seal. This involves the use of several members. In the first place, it is necessary to have the double faced adhesive tape and to remove protective strips from the adhesive surfaces before application. The tape is then spirally rolled onto the penis. After that the sheath is unrolled onto the tape and is pressed firmly against the tape to form a liquid tight seal. While the arrangement of the Hauser patent results in a liquid tight, relatively comfortable condom catheter, it has the drawback that considerable preparation is required in applying the condom catheter to the penis. Where a nurse or companion is applying this to a person, the time required and the ease of application is important. Also, if self-applied it is cumbersome to those with impaired dexterity.

In the Conway et al U.S. Pat. No. 4,475,910, the need for an adhesive tape underneath the sheath is eliminated. The sheath is provided with an adhesive on the inner surface. There is an adhesive release layer on the outer surface of the sheath so that when the sheath is in a rolled up condition, the turns of the roll do not adhere to each other. When the sheath is unrolled, the adhesive on the inner surface of the sheath causes the sheath to adhere firmly to the penis. This eliminates the need for a separate tape and greatly reduces the time and dexterity required to apply the condom catheter to the penis.

All of the arrangements of the prior art discussed above require a relatively long condom sheath which is initially rolled up and is then unrolled onto the penis. The unrolling of the sheath onto the penis has to be done carefully and again takes substantial time and dexterity. Moreover, any condom-type of sheath which covers much of the penile shaft leads to an increased risk of skin irritation and infection.

SUMMARY OF THE INVENTION

In the present invention, I employ a very short cone or cup-like sheath which does not extend beyond the head of the penis. This is in the form of a cup shaped portion connected to a tube leading to the urine receptacle. The cup shaped portion is of a shape to conform generally with that of the tip or glans of a typical penis. With this arrangement, all that it is necessary to do to apply the catheter to the penis is to press it over the head of the penis, making sure that the head or glans of the cup shaped portion firmly engages the wall of the penis. It thus becomes unnecessary to roll and unroll the catheter, as in prior devices.

The catheter preferably has a bulbous portion between the cup shaped portion and the tubular portion to minimize the possibility of flow being restricted when the catheter is bent and to receive any surges of urine. The opening from the cup shaped portion to the bulbous portion is preferably larger than the opening from the bulbous portion to the tubular portion so as to facilitate entry of the urine into the bulbous portion.

The Woodruff U.S. Pat. No. 822,099 shows a contraceptive condom which can be applied to the tip of a penis. There is no concept in this patent of using it as an external urine collection catheter and connecting it to a tubing which runs to a collection receptacle.

Further features of the invention will be apparent from a consideration of the accompanying specification, claims and drawing.

BRIEF DESCRIPTION OF THE DRAWINGS

FIG. 1 is a plan view of my improved urine collection catheter applied to a penis;

FIG. 2 is a view similar to FIG. 1 but showing the catheter and a connector and a portion of the discharge tube in section;

FIG. 3 is a sectional view on a slightly larger scale than FIG. 2 showing the catheter before it is applied to the penis and showing adhesive on the interior surface of the cup shaped portion of the urine collection catheter;

FIG. 4 is a view similar to FIG. 2 but showing a modified form of the invention; and FIG. 5 is a view similar to FIG. 3 but illustrating the modification of FIG. 4.

DETAILED DESCRIPTION OF THE PREFERRED EMBODIMENTS

The urine collection catheter of the present invention is indicated generally by the reference numeral 10. It is applied to the tip of a penis 11 and is fastened at its outer end to a connector 12 which in turn is connected to a tube 13 leading to any suitable urine receptacle (not shown).

The penis 11 is a typical penis having a penile shaft 14 and a somewhat conical head or glans 15.

Referring to the urine collection catheter of the present invention, it comprises three main portions. One is a conical portion 17, a bulbous portion 18 and an outer tubular portion 19. The entire catheter 10 is formed of a continuous piece of resilient material such as latex. The latex, after being applied to the mold in the desired thickness, is then cured, as is common to make the latex stable.

The outer end 19 of the catheter is connected to a connector 12 which is inserted into the tubular portion 19, as best shown in FIG. 2. The outer end of the connector is in turn connected to tubing 13 which, as previously referred to, leads to a urine receptacle. The conical portion 17 has a conical shape generally conforming with the tip of a typical penis. In one particular instance, the maximum diameter of the conical portion was about one inch, whereas the minimum outside diameter was about five-eights of an inch. As best shown in FIG. 3, the conical portion is coated on the inside with a suitable non-allergic pressure sensitive adhesive 22, such as an acrylic pressure sensitive adhesive.

Referring to the bulbous portion 18, this is formed of an inner conical wall 24 and a second outer conical wall 25 joined at an intermediate point 26. The junction of the inner conical wall 24 with the conical cap 17 is indicated by the reference numeral 28, and the junction of the outer conical wall with the tubular portion 19 by the reference character 29.

The bulbous portion 18 has two functions. In the first place, it tends to prevent obstruction of the fluid flow by kinking of the catheter. In the second place, because the internal diameter at point 28 is at least 25% higher than the internal diameter at point 26, the bulb 18 acts to absorb surges. When the urine comes out rapidly and there is a straight tubular portion from the conical cup shaped portion 17 through to 19, there is a tendency for the urine to back up. By providing the bulb shaped portion 18, this tendency is minimized. In a typical example, the interior diameter at point 28 was 0.460 inches and that at point 29 was 0.320 inches. It is, of course, also very important that the diameter at the apex 26 of the bulb shaped portion 18 be substantially greater than the interior diameter at point 28 or at point 29. This diameter should be at least 25% greater than the diameter at point 28. In a typical example, the interior diameter at apex 26 was 0.78 inches, whereas, as previously stated, the diameter at point 28 was 0.460 inches.

In the same example, the thickness of the material at the conical portion 17, the bulbous portion 18 and the tubular portion 19 was approximately 0.045 inches.

With the arrangement of FIGS. 1 through 3, the application of the urine collection catheter becomes extremely simple. The tip or glans of the penis must first be clean and dry. A suitable protective dressing may be applied to the tip to increase the holding power of the catheter. The unit is then taken out of its container with the adhesive 22 already present on the conical portion 17. All that is then necessary to do to apply it is to place the conical portion 17 over the tip of the penis and squeeze it slightly so that the adhesive is in firm engagement with the penis throughout the portion of the conical cup member 17 in engagement with the tip of the penis. It has been found that even though the cup 17 only engages the head or glans of the penis, a leak-proof seal is formed and the condom catheter adheres firmly to the penis despite flexing that might occur as the patient moves about. Obviously, the arrangement is much simpler to apply than where it is necessary to first apply a tape and then unroll a condom-type sheath over the tape as in known prior art catheters discussed above. it is unnecessary to roll or unroll any member and no auxiliary equipment such as adhesively coated tape is necessary to use.

When the catheter is to be removed, the upper edge is grasped to pull the catheter back off of the penis. Due to the fact that it extends only over the head of the penis, this can readily be done.

MODIFICATION OF FIGS. 4 AND 5

The modification of FIGS. 4 and 5 is identical to that of FIGS. 1 to 3 with the exception of the way in which the cup engaging the tip of the penis is formed. In order to enable comparison of the figures, the same reference characters are used for identical elements in the two forms of the invention. In the case of FIGS. 4 and 5, however, the cup which extends over the penis is indicated by the reference number 47 rather than 17.

It will be noted from FIGS. 4 and 5 that the wall thickness of the cup 47 is tapered. The thickness of the material is at its maximum at point 28 where it joins the bulb 18 and is at its minimum at the outer edge.

One advantage of the arrangement of FIGS. 4 and 5 is that it substantially eliminates the shoulder formed at the inner edge of the wall of member 17. This shoulder, designated in FIG. 2 by the numeral 32, constitutes an obstruction which can be engaged accidentally by a bedsheet or clothing so as to tend to loosen the conical cap 17 with respect to the penis. While the material of this conical cap 17 is relatively thin, as pointed out above, it still provides a sufficient shoulder that, under the right conditions, it could be engaged and tend to loosen the cap 17. With the tapered construction of cap 47, this is avoided.

It will be seen that I have provided a urine collection catheter in which it is possible to readily apply it to a penis with a minimum of preparatory work. The unit does not have to have a liner, as with some condom catheters. It does not have to be rolled and unrolled, as with most others. Furthermore, it retains many of the advantages of condom catheters which require more preparatory work. By reason of the bulb 18, any surges tend to be minimized. Furthermore, the obstruction of the flow by kinking is minimized.

Although the present invention has been described with reference to preferred embodiments, workers skilled in the art will recognize that changes may be made in form and detail without departing from the spirit and scope of the invention.

What is claimed is:

1. A urine collection catheter which is secured only to the tip of the penis and is formed of thin resilient material, the catheter having a tubular portion open at its outer end and designed to be connected to a urine receptacle and a cup shaped portion integrally connected to the inner end of said tubular portion, and forming the inner terminal part of said catheter, said cup shaped portion being of a shape and size to conform generally with that of the tip or glans of a typical penis, said cup shaped portion having a non-allergic pressure sensitive adhesive on the inner surface therof to enable said catheter to adhere to the tip of a penis in urine tight relation when the catheter is pressed into engagement with such tip to hold the tubular portion in urine conducting relation with the penis.

2. The urine collection catheter of claim 1 in which the cup shaped portion is conical.

3. The urine collection catheter of claim 1 in which there is a bulbous portion between the cup shaped portion and the tubular portion to receive surges of urine.

4. The urine collection catheter of claim 3 in which the opening from the cup shaped portion to the bulbous portion is larger than the opening from the bulbous portion to the tubular portion.

5. The urine collection catheter of claim 1 in which the thickness of the cup shaped portion decreases from its outer to its inner end.

6. The urine collection catheter of claim 3 in which the thickness of the tubular portion, the bulbous portion and the cup shaped portion adjacent its junction with the bulbous portion is approximately 0.045 inches.

* * * * *